US012723020B2

(12) United States Patent
Gornati et al.

(10) Patent No.: US 12,723,020 B2
(45) Date of Patent: Sep. 1, 2026

(54) PROCESS FOR PREPARING SOLRIAMFETOL HYDROCHLORIDE

(71) Applicant: Procos S.P.A., Cameri (IT)

(72) Inventors: Davide Gornati, Arluno (IT); Fabio Morana, Novara (IT); Jacopo Roletto, Turin (IT); Paolo Paissoni, Druento (IT)

(73) Assignee: Procos S.P.A., Cameri (IT)

(*) Notice: Subject to any disclaimer, the term of this patent is extended or adjusted under 35 U.S.C. 154(b) by 621 days.

(21) Appl. No.: 18/032,603

(22) PCT Filed: Oct. 19, 2021

(86) PCT No.: PCT/IB2021/059589
§ 371 (c)(1),
(2) Date: Apr. 19, 2023

(87) PCT Pub. No.: WO2022/084834
PCT Pub. Date: Apr. 28, 2022

(65) Prior Publication Data

US 2023/0391715 A1 Dec. 7, 2023

(30) Foreign Application Priority Data

Oct. 22, 2020 (IT) ........................ 102020000025042

(51) Int. Cl.

*C07C 269/04* (2006.01)
*C07C 59/50* (2006.01)
*C07C 213/08* (2006.01)
*C07C 213/10* (2006.01)
*C07C 227/36* (2006.01)
*C07C 227/40* (2006.01)
*C07C 229/36* (2006.01)

(52) U.S. Cl.

CPC ............ *C07C 269/04* (2013.01); *C07C 59/50* (2013.01); *C07C 213/08* (2013.01); *C07C 213/10* (2013.01); *C07C 227/36* (2013.01); *C07C 227/40* (2013.01); *C07C 229/36* (2013.01); *C07B 2200/07* (2013.01)

(58) Field of Classification Search

CPC ... C07C 269/08; C07C 271/12; C07C 227/40; C07C 229/36; C07C 213/00; C07C 215/28; C07C 213/10
USPC .......................................................... 560/163
See application file for complete search history.

(56) References Cited

FOREIGN PATENT DOCUMENTS

| | | |
|---|---|---|
| EP | 0133053 A1 | 2/1985 |
| WO | 2020035769 A1 | 2/2020 |

OTHER PUBLICATIONS

Hu, Z-Q. , et al., "Optical separation of racemic phenyl alanine and structure of complex consisting of *R*-phenyl alanine and *R*-mandelic acid", Chinese J. Struct. Chem., 23(1), 38-40 (2004).

*Primary Examiner* — Ana Z Muresan
(74) *Attorney, Agent, or Firm* — Elmore Patent Law Group, P.C.; Joseph C. Zucchero; Carolyn S. Elmore

(57) ABSTRACT

The present invention concerns a novel process for preparing solriamfetol hydrochloride.

8 Claims, 10 Drawing Sheets

PROCESS FOR PREPARING SOLRIAMFETOL HYDROCHLORIDE

FIELD OF THE INVENTION

The present invention concerns a novel process for preparing solriamfetol hydrochloride.

State of the Art

Solriamfetol, whose chemical name is (2R)-2-amino-3-phenylpropylcarbamate, is a drug used for the treatment of excessive sleepiness associated with narcolepsy and sleep apnea, and is marketed under the trade name Sunosi, in the form of the hydrochloride of formula (I)

(I)

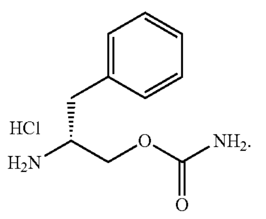

Different methods of synthesis of solriamfetol are known in the literature, which involve various intermediate products, such as D-phenylalanine, of formula (II), and D-phenylalaninol, i.e. (R)-(+)-2-amino-3-phenyl-1-propanol, of formula (III)

(II)

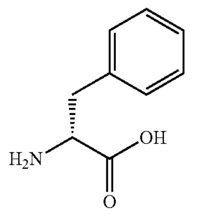

(III)

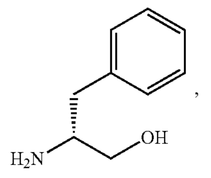

, which, for example, can be obtained starting from the corresponding amino acid of natural origin, L-phenylalanine, a compound of formula (IV)

(IV)

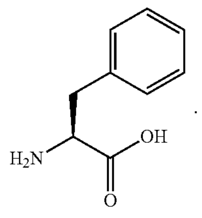

.

The Applicant found that the synthesis methods of solriamfetol, which provide for said intermediate products of formula (II) and (III), have technological limits linked to the difficulty of achieving high yields and competitive costs, also due to the chiral nature of the same being reversed with respect to the corresponding amino acid of natural origin, L-phenylalanine.

The Applicant found that the chiral nature of D-phenylalanine and D-phenylalaninol requires, in fact, the adoption of particular technical solutions in order to drive the stereospecificity of their preparation process, and that these particular technical solutions have a negative impact on the yield and on the overall costs of the synthesis of Solriamfetol hydrochloride.

SUMMARY OF THE INVENTION

The object of the present invention is therefore to provide a new process for the synthesis of solriamfetol hydrochloride capable of overcoming current difficulties and limits in obtaining the intermediates D-phenylalanine and D-phenylalaninol with high chemical and optical purity, thus reducing the impact on the yield and overall process costs of the final product.

According to the present invention, the Applicant has surprisingly found that it is possible to pursue the aforementioned object by using particular reaction conditions and expedients for obtaining the intermediates D-phenylalanine and D-phenylalaninol, starting from the corresponding starting amino acid of natural origin, L-phenylalanine.

In particular, the Applicant has discovered the possibility of obtaining in a simple way and in high yields a D-phenylalanine:(R)-mandelic acid complex with a particularly high diastereoisomeric ratio starting from L-phenylalanine. This allows the chirality of the latter to be substantially fully reversed in a single step, thus overcoming the current difficulties and limits in obtaining the intermediates D-phenylalanine and D-phenylalaninol, which can therefore be advantageously obtained with high optical and chemical purity, thus reducing their impact on the yield and overall costs of solriamfetol hydrochloride preparation. The process according to the present invention is therefore more competitive with respect to existing processes for the synthesis of solriamfetol hydrochloride.

Therefore, in a first aspect, the present invention relates to a process for preparing (2R)-2-amino-3-phenylpropylcarbamate hydrochloride of formula (I)

(I)

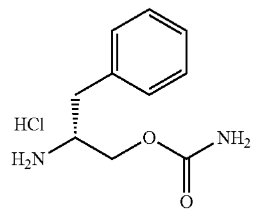

comprising the steps of:

a. adding (R)-mandelic acid and at least one aldehyde to a suspension of L-phenylalanine in acetic acid, thus obtaining a D-phenylalanine:(R)-mandelic acid complex, wherein the D-phenylalanine:(R)-mandelic acid molar ratio is 1:1;

b. isolating the D-phenylalanine of formula (II)

(II)

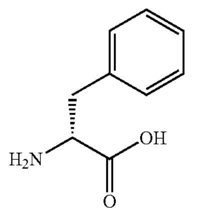

from the D-phenylalanine:(R)-mandelic acid complex obtained from step a;

c. reacting the D-phenylalanine obtained from step b. with a reducing agent, thus obtaining (R)-(+)-2-amino-3-phenyl-1-propanol of formula (III)

(III)

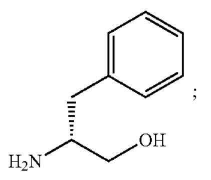

;

d. reacting (R)-(+)-2-amino-3-phenyl-1-propanol obtained from step c. with an acid thus obtaining (2R)-2-amino-3-phenylpropilcarbamate of formula (IV)

(IV)

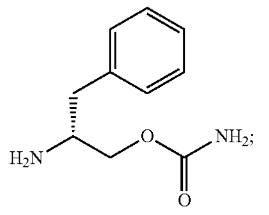

;

and e. converting (2R)-2-amino-3-phenylpropilcarbamate obtained from step d. into said (2R)-2-amino-3-phenylpropylcarbamate hydrochloride of formula (I).

In fact, it was surprisingly discovered that, thanks to the addition of (R)-mandelic acid and at least one aldehyde, it is possible to obtain in high yields a D-phenylalanine:(R)-mandelic acid complex with a particularly high diastereoisomeric ratio, starting from a suspension of L-phenylalanine in acetic acid.

Without being bound to a specific theory, the Applicant believes that the aldehyde reacts with the starting L-phenylalanine generating an imine species which, in the presence of acetic acid, leads to the formation of an iminium ion and racemization of its stereocenter, thus giving rise, after hydrolysis of the imine species, to in situ formation of the DL-phenylalanine racemic mixture. In the presence of mandelic acid, the D-phenylalanine thus formed reacts to form the D-phenylalanine:(R)-mandelic acid complex which, being slightly soluble in the reaction environment and also less soluble than the L-phenylalanine:(R)-mandelic acid complex, is easy to isolate. Furthermore, the hydrolysis of the imine species leads to regeneration of the starting aldehyde which is therefore not wasted during step a. and can further convert the L-phenylalanine remaining in the reaction medium, thereby progressing the dynamic kinetic resolution of the racemic mixture formed in situ and obtaining the D-phenylalanine:(R)-mandelic acid complex with a particularly high diastereoisomeric ratio.

This advantageously allows to effectively reverse the chirality of the starting L-phenylalanine in a single step, without any further particular technical solutions, in order to drive the stereospecificity of the reaction for obtaining D-phenylalanine and D-phenylalaninol, thus improving the process for preparing solriamfetol hydrochloride.

In a further aspect, the present invention also relates to a process for preparing a D-phenylalanine:(R)-mandelic acid complex, wherein the D-phenylalanine:(R)-mandelic acid molar ratio is 1:1, comprising the addition of (R)-mandelic acid and at least one aldehyde to a suspension of L-phenylalanine in acetic acid.

The advantages of the process for preparing said complex according to this further aspect have already been outlined with reference to the process according to the first aspect of the invention and are not replicated here.

The D-phenylalanine:(R)-mandelic acid complex obtained from the process according to the present invention, shows a particularly high diastereoisomeric ratio and therefore allows to obtain D-phenylalanine in high yields and in a simple way, thus representing a key intermediate in the synthesis of solriamfetol hydrochloride.

In a still further aspect, the present invention therefore also refers to a D-phenylalanine:(R)-mandelic acid complex, wherein the D-phenylalanine:(R)-mandelic acid molar ratio is 1:1, wherein said complex has a diastereoisomeric ratio higher than or equal to 99.5/0.5.

The high diastereoisomeric ratio of the complex according to this aspect of the invention represents, in fact, an advantage in preparing solriamfetol hydrochloride, as it allows to obtain D-phenylalanine and D-phenylalaninol with a high enantiomeric purity which, as observed by the Applicant, represent a key step for obtaining solriamfetol hydrochloride.

Therefore, in a further and advantageous aspect, the present invention also relates to a process for preparing D-phenylalanine of formula (II)

(II)

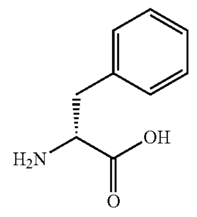

comprising the steps of:

i. adding (R)-mandelic acid and at least one aldehyde to a suspension of L-phenylalanine in acetic acid, thus obtaining a D-phenylalanine:(R)-mandelic acid complex, wherein the D-phenylalanine:(R)-mandelic acid molar ratio is 1:1; and ii. isolating D-phenylalanine from the D-phenylalanine:(R)-mandelic acid complex obtained from step i.

The advantages of the process for preparing D-phenylalanine according to this further aspect have already been outlined with reference to the process according to the first aspect of the invention and are not replicated here. D-phenylalanine represents a key intermediate product for the synthesis of solriamfetol hydrochloride and the Applicant has found that an improved process for obtaining it can therefore contribute to making the synthesis of solriamfetol hydrochloride more competitive than existing processes.

In a further and advantageous aspect, the present invention also relates to a process for preparing (R)-(+)-2-amino-3-phenyl-1-propanol of formula (III)

(III)

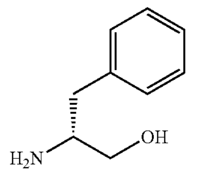

comprising the steps of:

1. adding (R)-mandelic acid and at least one aldehyde to a suspension of L-phenylalanine in acetic acid, thus obtaining a D-phenylalanine:(R)-mandelic acid complex, wherein the D-phenylalanine:(R)-mandelic acid molar ratio is 1:1;
2. isolating D-phenylalanine from the D-phenylalanine:(R)-mandelic acid complex obtained from step 1.;
3. reacting the D-phenylalanine obtained from step 2. with a reducing agent, thus obtaining said (R)-(+)-2-amino-3-phenyl-1-propanol of formula (III).

The advantages of the process for preparing (R)-(+)-2-amino-3-phenyl-1-propanol (D-phenylalaninol) according to this further aspect have already been outlined with reference to the process according to the first aspect of the invention and are not replicated here. D-phenylalaninol represents a key intermediate product for the synthesis of solriamfetol hydrochloride and the Applicant has found that an improved process for obtaining it can therefore contribute to making the synthesis of solriamfetol hydrochloride more competitive than existing processes.

DETAILED DESCRIPTION OF THE INVENTION

Figure 1:
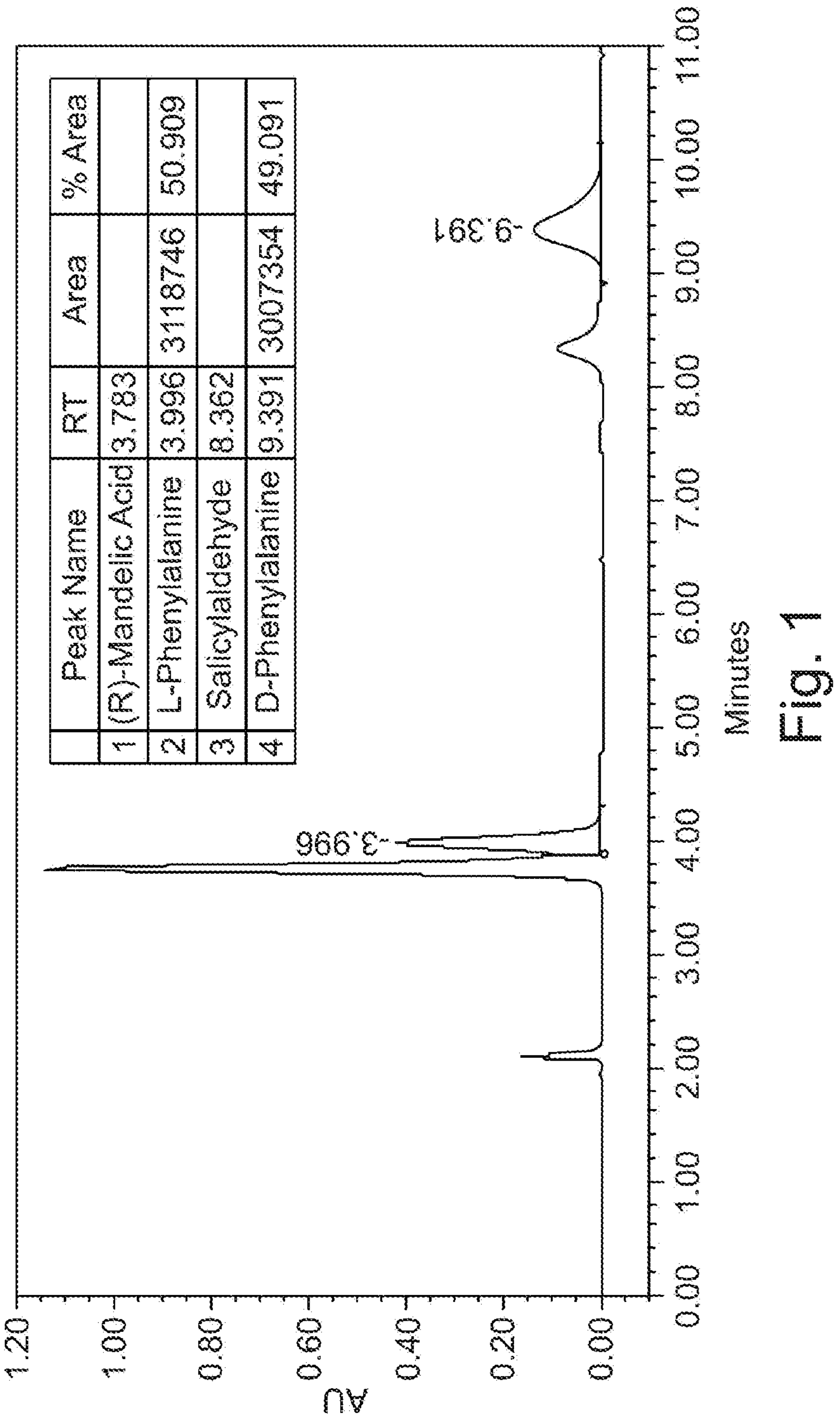
FIG. 1 shows the HPLC chromatogram of the reaction mixture of Example 1.

In a first aspect, the present invention relates to a process for preparing (2R)-2-amino-3-phenylpropylcarbamate hydrochloride of formula (I)

(I)

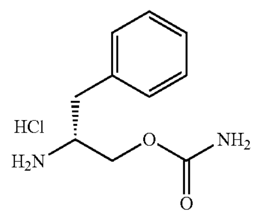

comprising the steps of:

a. adding (R)-mandelic acid and at least one aldehyde to a suspension of L-phenylalanine in acetic acid, thus obtaining a D-phenylalanine:(R)-mandelic acid complex, wherein the D-phenylalanine:(R)-mandelic acid molar ratio is 1:1;

b. isolating the D-phenylalanine of formula (II)

(II)

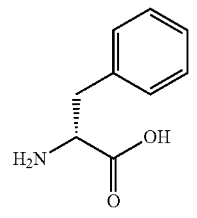

from the D-phenylalanine:(R)-mandelic acid complex obtained from step a;

c. reacting the D-phenylalanine obtained from step b. with a reducing agent, thus obtaining (R)-(+)-2-amino-3-phenyl-1-propanol of formula (III)

(III)

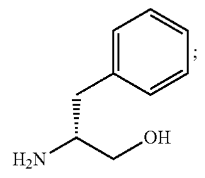

;

d. reacting (R)-(+)-2-amino-3-phenyl-1-propanol obtained from step c. with an acid thus obtaining (2R)-2-amino-3-phenylpropilcarbamate of formula (IV)

(IV)

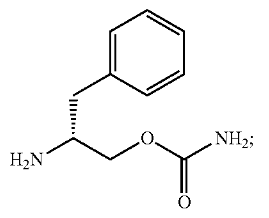

and e. converting (2R)-2-amino-3-phenylpropilcarbamate obtained from step d. into said (2R)-2-amino-3-phenylpropylcarbamate hydrochloride of formula (I).

In fact, it was surprisingly discovered that, thanks to the addition of (R)-mandelic acid and at least one aldehyde, it is possible to obtain in high yields a D-phenylalanine:(R)-mandelic acid complex with a particularly high diastereoisomeric ratio, starting from a suspension of L-phenylalanine in acetic acid.

Without being bound to a specific theory, the Applicant believes that the aldehyde reacts with the starting L-phenylalanine generating an imine species which, in the presence of acetic acid, leads to the formation of an iminium ion and to racemization of its stereocenter, thus giving rise, after hydrolysis of the imine species, to the in situ formation of the DL-phenylalanine racemic mixture. In the presence of mandelic acid, the D-phenylalanine thus formed reacts to form the D-phenylalanine:(R)-mandelic acid complex which, being poorly soluble in the reaction environment and also less soluble than the L-phenylalanine:(R)-mandelic acid complex, is easy to isolate. Furthermore, the hydrolysis of the imine species leads to regeneration of the starting aldehyde which is therefore not wasted during step a. and can further convert the L-phenylalanine remaining in the reaction medium, thereby progressing the dynamic kinetic resolution of the racemic mixture formed in situ, and obtaining the D-phenylalanine:(R)-mandelic acid complex with a particularly high diastereoisomeric ratio.

This advantageously allows to effectively reverse the chirality of the starting L-phenylalanine in a single step, without any further particular technical solutions in order to drive the stereospecificity of the reaction for obtaining D-phenylalanine and D-phenylalaninol, thus improving the process for preparing solriamfetol hydrochloride.

Within the scope of the present description and in the subsequent claims, all numerical quantities indicating amounts, parameters, percentages, and so on, are to be intended in all circumstances as preceded by the term "about", unless otherwise stated. Furthermore, all ranges of numerical quantities include all possible combinations of the maximum and minimum numerical values and all possible intermediate ranges, in addition to those specifically indicated below.

Within the scope of the present description and in the subsequent claims, the expression "diastereoisomeric ratio" (also abbreviated "d.r.") means the molar ratio between the D-phenylalanine:(R)-mandelic acid complex and the L-phenylalanine:(R)-mandelic acid complex, expressed as D-phenylalanine:(R)-mandelic acid complex/L-phenylalanine:(R)-mandelic acid complex. For example, a diastereoisomeric ratio of 99.5/0.5 indicates a product in which 99.5 parts by moles of D-phenylalanine:(R)-mandelic acid complex and 0.5 parts by moles of L-phenylalanine:(R)-mandelic acid complex are present.

The present invention may present in one or more of its aspects one or more of the preferred characteristics reported hereinafter, which can be combined with each other according to the application requirements.

The process according to the present invention comprises the step a. of adding (R)-mandelic acid and at least one aldehyde to a suspension of L-phenylalanine in acetic acid, thus obtaining a D-phenylalanine:(R)-mandelic acid complex, wherein the D-phenylalanine:(R)-mandelic acid molar ratio is 1:1.

Preferably, in said step a., said at least one aldehyde is selected from the group consisting of salicylaldehyde, benzaldehyde, picolinaldehyde (2-formyl pyridine), isonicotinaldehyde (4-formyl pyridine), propionaldehyde, and butyraldehyde.

In a preferred embodiment, in said step a., said at least one aldehyde is salicylaldehyde.

Preferably, in said step a, from 1 to 1.75 equivalents of (R)-mandelic acid per 1 equivalent of L-phenylalanine, more preferably from 1.1 to 1.6 equivalents of (R)-mandelic acid per 1 equivalent of L-phenylalanine are added.

Preferably, in said step a, from 0.01 to 0.2 equivalents of said at least one aldehyde per 1 equivalent of L-phenylalanine, more preferably from 0.01 to 0.15 equivalents of said at least one aldehyde per 1 equivalent of L-phenylalanine are added.

Preferably, in said step a., said dispersion of L-phenylalanine in acetic acid, comprises from 12% to 25% by weight of L-phenylalanine, with respect to the weight of acetic acid.

Preferably, said step a. is carried out at a temperature between 10° C. and 80° C.

Preferably, said step a. it is carried out without adding water. Although step a. may also be carried out in the presence of water, the Applicant has in fact observed that water slows down the reaction kinetics in step a., making the process less productive.

Preferably, in said step a., the mixture is kept under stirring at a temperature ranging from 50° C. to 70° C., preferably for a time ranging from 1 hour to 10 hours. Subsequently, the mixture thus obtained is then preferably brought to a temperature ranging from 15° C. to 30° C., preferably over a period of time ranging from 1.5 hours to hours, and then kept at said temperature, under stirring, for a time ranging from 40 hours to 150 hours.

Preferably, said step a. comprises isolating said D-phenylalanine:(R)-mandelic acid complex from the reaction mixture.

Preferably, said isolating step comprises at least one operation selected from the group consisting of washing with acetic acid, filtering, and drying said D-phenylalanine:(R)-mandelic acid complex.

Preferably said drying step is carried out at a temperature ranging from 30° C. to 50° C., preferably for a time ranging from 15 to 35 hours.

The process according to the present invention comprises the step b. of isolating the D-phenylalanine of formula (II)

(II)

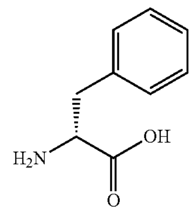

from the D-phenylalanine:(R)-mandelic acid complex obtained from step a.

The D-phenylalanine:(R)-mandelic acid complex obtained from said step a. advantageously shows a D-phenylalanine:(R)-mandelic acid molar ratio of 1:1, and preferably a diastereoisomeric ratio (d.r.) higher than or equal to 98/2, even more preferably higher than or equal to 99.5/0.5.

Said diastereoisomeric ratio may be determined by chiral HPLC analysis.

Preferably, said step b. is carried out at a temperature between 10° C. and 60° C.

Preferably, said step b. comprises adding at least one base to a solution of said complex in at least one polar solvent.

The Applicant has in fact also surprisingly discovered that, thanks to the addition of at least one base to a solution of a D-phenylalanine:(R)-mandelic acid complex in at least one protic solvent, wherein the molar ratio D-phenylalanine:(R)-mandelic acid is 1:1, it is possible to isolate D-phenylalanine in high yields. This advantageously allows to easily have an ideal starting product for the reaction of obtaining D-phenylalaninol, thus improving the process for preparing solriamfetol hydrochloride.

Preferably, in said step b., said at least one base is selected from the group consisting of an amine, aqueous ammonia.

Preferably, in said step b., said amine is selected from the group consisting of triethylamine, diisopropylethylamine, more preferably said amine is triethylamine.

Preferably, in said step b., said at least one base is added to said solution at a temperature ranging from 15° C. to 40° C., preferably over a period of time ranging from minutes to 2 hours.

Preferably, in said step b, from 1 to 2 equivalents, more preferably from 1.05 to 1.2 equivalents, of said at least one base per 1 equivalent of said complex are added.

Preferably, in said step b., said at least one polar solvent is protic, more preferably selected from the group consisting of water, methanol, ethanol, iso-propanol, n-propanol.

Preferably, in said step b., said at least one polar solvent is a binary water/ethanol mixture.

Preferably, in said step b., once the addition of said base is completed, the mixture thus obtained is kept under stirring at a temperature ranging from 15° C. to 30° C., preferably for a time ranging from 2 hours to 6 hours. Subsequently, in said phase b., the mixture thus obtained is preferably filtered and the D-phenylalanine thus separated is washed with at least one polar solvent and dried.

Preferably, said at least one polar solvent is selected from the group consisting of water, methanol, ethanol, iso-propanol, n-propanol.

Preferably, D-phenylalanine is dried at a temperature ranging from 30° C. to 50° C., preferably for a time ranging from 50 hours to 100 hours.

Withing the scope of the present description and subsequent claims, the expression "chemical purity" means the relationship between a product and related substances, and the expression "optical purity" means the relationship between a product and its enantiomer.

At the end of step b. of the process according to the present invention, it is possible to obtain said D-phenylalanine with an optical purity >99.5/0.5, i.e. a product wherein the molar ratio D-phenylalanine/L-phenylalanine is greater than 99.5/0.5.

The process according to the present invention comprises the step c. of reacting the D-phenylalanine obtained from step b. with a reducing agent, thus obtaining (R)-(+)-2-amino-3-phenyl-1-propanol of formula (III)

(III)

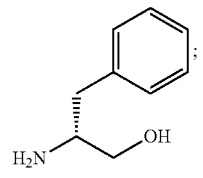

Preferably, said step c. comprises reacting the D-phenylalanine obtained from step b. with a reducing system consisting of sodium borohydride and boron trifluoride, wherein said sodium borohydride is used in amounts ranging from 1 to 1.2 equivalent with respect to said D-phenylalanine.

The Applicant has, in fact, also surprisingly discovered that it is possible to effectively reduce D-phenylalanine to D-phenylalaninol ((R)-(+)-2-amino-3-phenyl-1-propanol) by using a reducing system consisting of sodium borohydride and boron trifluoride, wherein said sodium borohydride is added in limited and specific amounts with respect to the D-phenylalanine to be reduced. The combined use of sodium borohydride and boron trifluoride allows the formation, even in situ, of borane species capable of reducing D-phenylalanine to D-phenylalaninol, and the use of limited amounts of sodium borohydride with respect to D-phenylalanine reduces significantly, and almost completely eliminates, the formation of hydrogen in the reaction medium. At the same time, this eliminates the safety issues associated with the presence of a flammable gas and allows a better control of the reaction for obtaining D-phenylalaninol, thus improving the process for preparing solriamfetol hydrochloride.

Preferably, in said step c., said D-phenylalanine is suspended in at least one aprotic solvent.

Preferably, said at least one aprotic solvent is tetrahydrofuran (THF).

Preferably, said at least one aprotic solvent is anhydrous.

Preferably, in said step c., said sodium borohydride is used in amounts ranging from 1.05 to 1.15 equivalents per 1 equivalent of said D-phenylalanine.

Preferably, in said step c., said boron trifluoride is used in amounts ranging from 1.7 to 3.0 equivalent with respect to 1 equivalent of said D-phenylalanine.

Preferably, in said step c., said sodium borohydride and said boron trifluoride are added to the reaction mixture separately.

In one embodiment, said sodium borohydride is added before said boron trifluoride.

In a further embodiment, said boron trifluoride is added before said sodium borohydride.

Preferably, when the reducing agent is a reducing system consisting of sodium borohydride and boron trifluoride, said step c. is carried out at a temperature between ° C. and 60° C.

Preferably, in said step c., said sodium borohydride and said boron trifluoride are added to D-phenylalanine at a temperature ranging from 30 to 40° C., preferably over a period of time ranging from 2 to 10 hours.

Preferably, in said step c., after completing the addition of the reducing agent, the reaction mixture is kept under stirring at a temperature ranging from 30° C. to 40° C., preferably for a time ranging from 2 to 10 hours.

Subsequently, water is added in said step c. Said addition of water quenches the reaction and then a basic aqueous solution is advantageously added, more preferably an aqueous solution of an alkaline or alkaline earth metal hydroxide, more preferably sodium hydroxide. Preferably, the addition of said aqueous solution of an alkaline or alkaline earth metal hydroxide is carried out over a period of time ranging from 1 to 5 hours.

Preferably, said step c. comprises isolating said (R)-(+)-2-amino-3-phenyl-1-propanol.

Preferably, said isolating step comprises extracting with an organic solvent and crystallizing said (R)-(+)-2-amino-3-phenyl-1-propanol.

Preferably, said organic solvent is selected from the group consisting of 2-methyltetrahydrofuran (MeTHF), dichloromethane, iso-butanol, normal-butanol, toluene, isopropyl acetate, ethyl acetate, tert-butyl acetate, tetrahydrofuran.

In a preferred embodiment, said step c. comprises crystallizing said D-phenylalaninol. Preferably said crystallization is carried out by dissolution of D-phenylalaninol from step c. in a solvent, advantageously in toluene, and subsequent precipitation of D-phenylalaninol by cooling.

The Applicant has in fact surprisingly found that, in this way, it is possible to obtain D-phenylalaninol in particularly high yield, chemical purity, and optical purity.

At the end of step c. of the process according to the present invention, it is possible to obtain said D-phenylalaninol with an optical purity >99.9/0.1, i.e. a product wherein the molar ratio between D-phenylalaninol and L-phenylalaninol is higher than 99.9/0.1.

The process according to the present invention comprises the step d. of reacting (R)-(+)-2-amino-3-phenyl-1-propanol obtained from step c. with an acid, thus obtaining (2R)-2-amino-3-phenylpropylcarbamate of formula (IV)

(IV)

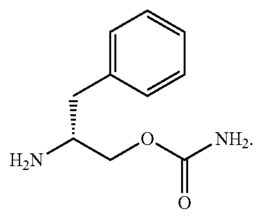

Preferably, said step d. is carried out at a temperature between −10° C. and 30° C.

Preferably, in said step d., the reaction between (R)-(+)-2-amino-3-phenyl-1-propanol obtained from step c. and an acid occurs in an anhydrous organic solvent.

Preferably, in said step d., said acid is generated in situ by the reaction between a cyanate and a strong acid.

Preferably said cyanate is an alkali metal cyanate, even more preferably sodium cyanate.

Preferably, said strong acid is anhydrous.

Preferably, in said step d., said strong anhydrous acid is added over a period of time ranging from 2 hours to 4 hours. Preferably, during said addition the reaction mixture is kept at a temperature ranging from −10° C. to 5° C.

Preferably, said strong acid is selected from the group consisting of methanesulfonic acid, hydrochloric acid.

Preferably, in said step d., said strong acid is used in amounts ranging from 3 to 10 equivalents per 1 equivalent of (R)-(+)-2-amino-3-phenyl-1-propanol.

Preferably, in said step d., said anhydrous organic solvent is dichloromethane.

Preferably, in said step d., said acid is mixed with (R)-(+)-2-amino-3-phenyl-1-propanol in the presence of an anhydrous organic solvent, under stirring at a temperature ranging from −10° C. to 5° C. Preferably said acid is added to a solution of (R)-(+)-2-amino-3-phenyl-1-propanol in said anhydrous organic solvent.

Preferably, to terminate the reaction, a basic aqueous solution is added to bring the mixture to a pH greater than 10, more preferably an aqueous solution of an alkaline or alkaline earth metal hydroxide, more preferably sodium hydroxide.

Preferably, said step d. comprises isolating said (2R)-2-amino-3-phenylpropylcarbamate from the reaction mixture.

Preferably, said isolating step comprises at least one operation selected from the group consisting of extracting with an organic solvent, washing, filtering, drying, and concentrating said (2R)-2-amino-3-phenylpropylcarbamate.

Preferably, said organic solvent is selected from the group consisting of dichloromethane, MeTHF, iso-butanol, normal-butanol, toluene, isopropyl acetate, ethyl acetate, tert-butyl acetate, tetrahydrofuran.

The process according to the present invention comprises the step e. of converting the (2R)-2-amino-3-phenylpropylcarbamate obtained from step d. into ((2R)-2-amino-3-phenylpropylcarbamate hydrochloride of formula (I)

(I)

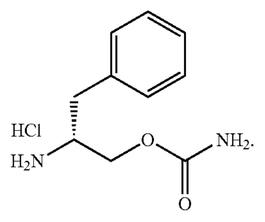

Preferably, said step e. comprises bubbling gaseous HCl into a solution of said (2R)-2-amino-3-phenylpropylcarbamate in a polar protic solvent.

Preferably, in said step e., said polar protic solvent is selected from the group consisting of an alcohol.

Preferably, said alcohol is isopropanol.

Preferably, in said step e., said polar protic solvent is anhydrous.

Preferably, in said step e., said bubbling of gaseous HCl is carried out at a temperature below 60° C.

Preferably, in said step e., the mixture thus obtained is kept under stirring at a temperature ranging from 20° C. to 60° C., preferably for a time ranging from 1 hour to hours.

Preferably, said step e. comprises isolating said (2R)-2-amino-3-phenylpropylcarbamate hydrochloride from the reaction mixture.

Preferably, said isolating step comprises at least one operation selected from the group consisting of washing with an aprotic polar solvent, filtering, and drying said (2R)-2-amino-3-phenylpropylcarbamate hydrochloride.

Preferably, said polar protic solvent is isopropanol.

Preferably, said drying is carried out under vacuum, at a pressure from 0 to 10 mBar, at a temperature from 25 to 40° C.

In a further aspect, the present invention further relates to a process for preparing a D-phenylalanine:(R)-mandelic acid complex, wherein the D-phenylalanine:(R)-mandelic acid molar ratio is 1:1, comprising the addition of (R)-mandelic acid and at least one aldehyde to a suspension of L-phenylalanine in acetic acid.

The advantages of the process for preparing said complex according to this further aspect have already been outlined with reference to the process according to the first aspect of the invention and are not replicated here.

Preferably, the process for preparing the D-phenylalanine:(R)-mandelic acid complex according to the present invention may have one or more of the preferred characteristics of step a. of the process for preparing (2R)-2-amino-3-phenylpropylcarbamate hydrochloride according to the first aspect of the present invention, which can be combined with each other according to the application requirements.

The D-phenylalanine:(R)-mandelic acid complex obtained from the process according to the present invention shows a particularly high diastereoisomeric ratio, and therefore allows to obtain D-phenylalanine in high yields and in a simple way, representing therefore a key intermediate in the synthesis of solriamfetol hydrochloride.

In a still further aspect, the present invention therefore also refers to a D-phenylalanine:(R)-mandelic acid complex, wherein the D-phenylalanine:(R)-mandelic acid molar ratio is 1:1, wherein said complex has a diastereoisomeric ratio higher than or equal to 99.5/0.5.

The high diastereoisomeric ratio of the complex according to this aspect of the invention represents, in fact, an advantage for the preparation of solriamfetol hydrochloride, as it allows to obtain D-phenylalanine and D-phenylalaninol having high enantiomeric purity, which, as found by the Applicant, represent a key step for obtaining solriamfetol hydrochloride.

Therefore, in a further and advantageous aspect, the present invention also relates to a process for preparing D-phenylalanine of formula (II)

(II)

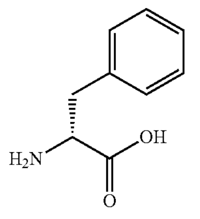

comprising the steps of:

i. adding (R)-mandelic acid and at least one aldehyde to a suspension of L-phenylalanine in acetic acid, thus obtaining a D-phenylalanine:(R)-mandelic acid complex, wherein the D-phenylalanine:(R)-mandelic acid molar ratio is 1:1; and
ii. isolating D-phenylalanine from the D-phenylalanine:(R)-mandelic acid complex obtained from step i.

The advantages of the process for preparing D-phenylalanine according to this further aspect have already been outlined with reference to the process according to the first aspect of the invention and are not replicated here. D-phenylalanine represents a key intermediate product for the synthesis of solriamfetol hydrochloride, and the Applicant has found that an improved process for obtaining it can therefore contribute to making the synthesis of solriamfetol hydrochloride more competitive with respect to existing processes.

Preferably, step i. of the process for preparing D-phenylalanine according to the present invention may have one or more of the preferred characteristics respectively of step a. of the process for preparing (2R)-2-amino-3-phenylpropylcarbamate hydrochloride according to the first aspect of the present invention, which can be combined with each other according to the application requirements.

Preferably, step ii. of the process for preparing D-phenylalanine according to the present invention may have one or more of the preferred characteristics respectively of step b. of the process for preparing (2R)-2-amino-3-phenylpropylcarbamate hydrochloride according to the first aspect of the present invention, which can be combined with each other according to the application requirements.

In a further and advantageous aspect, the present invention also relates to a process for preparing (R)-(+)-2-amino-3-phenyl-1-propanol of formula (III)

(III)

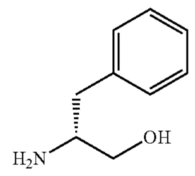

comprising the steps of:

1. adding (R)-mandelic acid and at least one aldehyde to a suspension of L-phenylalanine in acetic acid, thus obtaining a D-phenylalanine:(R)-mandelic acid complex, wherein the D-phenylalanine:(R)-mandelic acid molar ratio is 1:1;
2. isolating D-phenylalanine from the D-phenylalanine:(R)-mandelic acid complex obtained from step 1.; and
3. reacting D-phenylalanine obtained from step 2. with a reducing agent, thus obtaining said (R)-(+)-2-amino-3-phenyl-1-propanol of formula (III).

The advantages of the process for preparing (R)-(+)-2-amino-3-phenyl-1-propanol (D-phenylalaninol) according to this further aspect have already been outlined with reference to the process according to the first aspect of invention and are not replicated here. D-phenylalaninol represents a key intermediate product for the synthesis of solriamfetol hydrochloride, and the Applicant has found that an improved process for obtaining it can therefore contribute to making the synthesis of Solriamfetol hydrochloride more competitive with respect to existing processes.

Preferably, step 1. of the process for preparing (R)-(+)-2-amino-3-phenyl-1-propanol according to the present invention may have one or more of the preferred characteristics respectively of step a. of the process for preparing (2R)-2-amino-3-phenylpropylcarbamate hydrochloride according to the first aspect of the present invention, which can be combined with each other according to the application requirements.

Preferably, step 2. of the process for preparing (R)-(+)-2-amino-3-phenyl-1-propanol according to the present invention may have one or more of the preferred characteristics respectively of step b. of the process for preparing (2R)-2-amino-3-phenylpropylcarbamate hydrochloride according to the first aspect of the present invention, which can be combined with each other according to the application requirements.

Preferably, step 3. of the process for preparing (R)-(+)-2-amino-3-phenyl-1-propanol according to the present invention may have one or more of the preferred characteristics respectively of step c. of the process for preparing (2R)-2-amino-3-phenylpropylcarbamate hydrochloride according to the first aspect of the present invention, which can be combined with each other according to the application requirements.

The invention will be now illustrated by means of some Examples to be intended for illustrative and not limitative purposes of the same.

EXPERIMENTAL PART

Methods

Chiral HPLC analysis: to perform the analysis, the sample is dissolved at a concentration of 2 milligrams/milliliter in a solution consisting of 80 parts by volume of a solution of perchloric acid at 0.1% by volume in water and 20 parts by volume of acetonitrile, and is then analyzed according to the following method:

HPLC chromatograph with UV detector;
Column: CROWPAK CR I (−), 150×5.0 mm, 5p
Column temperature: 25° C.
Eluent: Mobile phase A=Buffer (100%), Buffer: perchloric acid at 0.1% by volume in water; Mobile phase B=Acetonitrile;
Gradient: Isocratic 80:20 NB hold for 11 minutes;
Eluent Flow Rate: 0.4 mL/min;
Injected volume 5 microliters; and
UV Detection wavelength: 215 nm.

1H NMR: spectra were recorded with a BRUKER AV400 instrument in DMSO-d6. 50 microliters of trifluoroacetic acid were added to the samples in order to salsify the amines present in the structure.

EXAMPLES

Example 1—Preparation of D-Phenylalanine:(R)-Mandelic Acid Complex 1.12 grams of salicylaldehyde (9.2 mmol, 0.05 eq) were added to a suspension of L-phenylalanine (30.4 g, 184.0 mmol, 1 eq) and (R)-mandelic acid (42. g, 276.1 mmol, 1.5 eq) in 122 mL of acetic acid. The reaction mixture was heated to 60° C. and stirred at the same temperature for 3 hours until almost complete racemization, as determined by chiral HPLC analysis according to the method described above. After one hour of reaction, the complete dissolution of the reagents was observed.

FIG. 1 shows the HPLC chromatogram obtained after complete dissolution of the reagents, in which the peaks related to (L)-phenylalanine (RT 3.996) and (D)-phenylalanine (RT 9.391) of the obtained racemic mixture are identifiable.

The reaction mixture was then allowed to spontaneously cool to 22° C. for 3 hours, then stirred at the same temperature for a further 66 hours. The formation of a precipitate was observed about 30 minutes after reaching the temperature of 22° C.

The reaction mixture thus obtained was then filtered; the solid was washed with acetic acid (30 mL) and dried at 40° C. for 24 hours. A D-phenylalanine:(R)-Mandelic Acid complex (54.0 g, 92% yield, diastereoisomeric ratio (d.r.) >99.5/0.5) was obtained as a white solid.

The product thus obtained was analyzed by chiral HPLC and 1H NMR, showing no more than 0.5% of L-phenylalanine.

Figure 2:
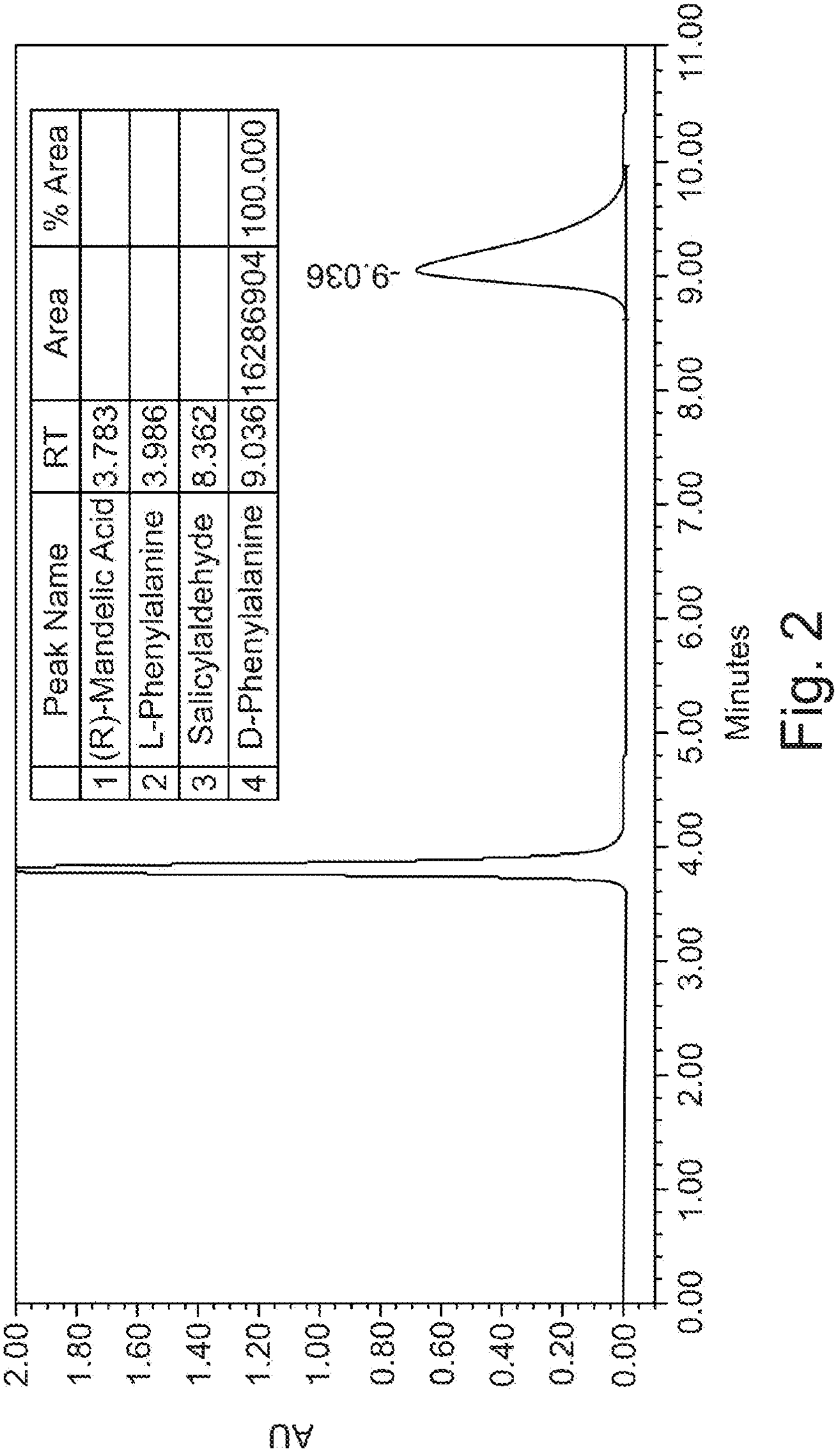
FIG. 2 shows the HPLC chromatogram of the D-phenylalanine:(R)-mandelic acid complex obtained according to Example 1.

FIG. 2 shows the HPLC chromatogram obtained, in which there is the peak corresponding to (D)-phenylalanine (RT 9.039) and the substantial disappearance of the peak related to (L)-phenylalanine, thus confirming the inversion with respect to the start of the reaction.

Figure 3:
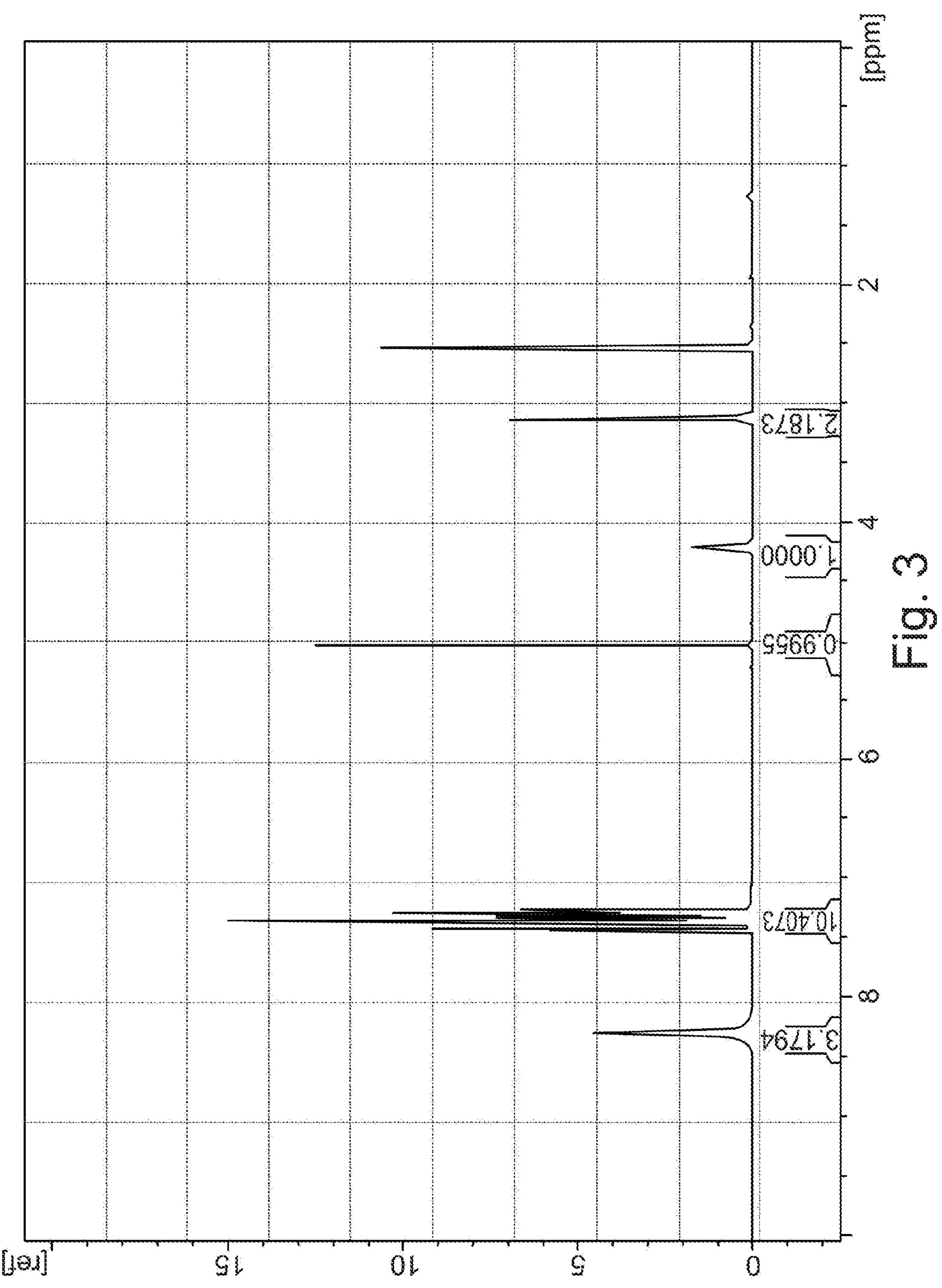
FIG. 3 shows the 1H NMR spectrum of the D-phenylalanine:(R)-mandelic acid complex according to Example 1.

FIG. 3 shows the obtained 1H NMR spectrum (300 MHz, DMSO-d6+TFA) which allows to confirm the D-phenylalanine:(R)-mandelic acid molar ratio of 1:1. The following is the assignment of the related peaks: δ (ppm) 8.29 (bs, 3H, NH), 7.43-7.24 (m, 10H), 5.02 (s, 1H), 4.19 (m, 1H), 3.10 (m, 2H).

Example 2—Preparation of D-Phenylalanine:(R)-Mandelic Acid Complex 0.55 grams of salicylaldehyde (4.5 mmol, 0.05 eq) were added to a suspension of L-phenylalanine (15.1 g, 91.0 mmol, 1 eq) and (R)-mandelic acid (15.8 g, 104.4 mmol, 1.14 eq) in 160 milliliters of acetic acid. The reaction mixture was heated to 60° C. and stirred at the same temperature for 90 minutes until almost complete racemization was detected by chiral HPLC analysis according to the method described above. The reaction mixture was then allowed to spontaneously cool to 22° C. for 3 hours, then stirred at the same temperature for a further 72 hours. The reaction mixture was filtered, the solid was washed with acetic acid (15 mL) and dried at 40° C. for 24 hours. A D-phenylalanine:(R)-mandelic acid complex was obtained as a white solid (23.5 g, 82% yield, d.r. 98.5/1.5), whose identification and characterization by HPLC and 1H NMR was carried out according to the methods described above, obtaining results fully similar to those of the second complex of Example 1.

Example 3—Preparation of D-Phenylalanine:(R)-Mandelic Acid Complex 1.52 grams of salicylaldehyde (12.5 mmol, 0.13 eq) were added to a suspension of L-phenylalanine (15.0 g, 91.0 mmol, 1 eq) and (R)-mandelic acid (15.9 g, 104.4 mmol, 1.15 eq) in 75 milliliters of acetic acid. The reaction mixture was heated to 60° C. and stirred at the same temperature for 90 minutes until almost complete racemization was detected by chiral HPLC analysis according to the method described above. The reaction mixture was allowed to spontaneously cool to 22° C. for 3 hours, then stirred at the same temperature for a further 72 hours. About 3 hours after reaching the temperature of 22° C. the formation of a precipitate was observed. The reaction mixture was then filtered, the solid was washed with acetic acid (15 mL) and dried at 40° C. for 24 hours. A D-phenylalanine-mandelic acid (R) complex was obtained as a white solid (21.0 g, 74% yield, d.r. 98/2), whose identification and characterization by HPLC and 1H NMR was carried out according to the methods described above, obtaining results fully similar to those of the second complex of Example 1.

Example 4—Preparation of D-Phenylalanine:(R)-Mandelic Acid Complex grams of salicylaldehyde (0.6 mmol, 0.01 eq) were added to a suspension of L-phenylalanine (10.1 g, 61.0 mmol, 1 eq) and (R)-mandelic acid (10.5 g, 69.1 mmol, 1.15 eq) in 50 milliliters of acetic acid. The reaction mixture was heated to 60° C. and stirred at the same temperature for 9 hours until almost complete racemization was detected by chiral HPLC analysis according to the method described above. The reaction mixture was allowed to spontaneously cool to 22° C. for 3 hours, then stirred at the same temperature for a further 136 hours. The reaction mixture was filtered, the solid was washed with acetic acid (10 mL) and dried at 40° C. for 24 hours. A D-phenylalanine-mandelic acid (R) complex was obtained as a white solid (14.0 g, 74% yield, d.r. 98/2), whose identification and characterization by HPLC and 1H NMR was carried out according to the methods described above, obtaining results fully similar to those of the second complex of Example 1.

Example 5—Synthesis of D-Phenylalanine 18.9 grams of triethylamine (187.2 mmol) were slowly added, over 1 hour, to a suspension of D-phenylalanine:(R)-mandelic acid complex according to Example 1 (54.0 g, 170.2 mmol, 1 eq) in 270 mL of an EtOH/water mixture (95:5 v/v), while keeping the temperature between 20 and 30° C. After the addition was complete, the mixture was stirred at 25° C. for 4 hours and then filtered; the solid was washed with EtOH (2×40 mL) and dried at 40° C. for 72 hours.

Figure 4:
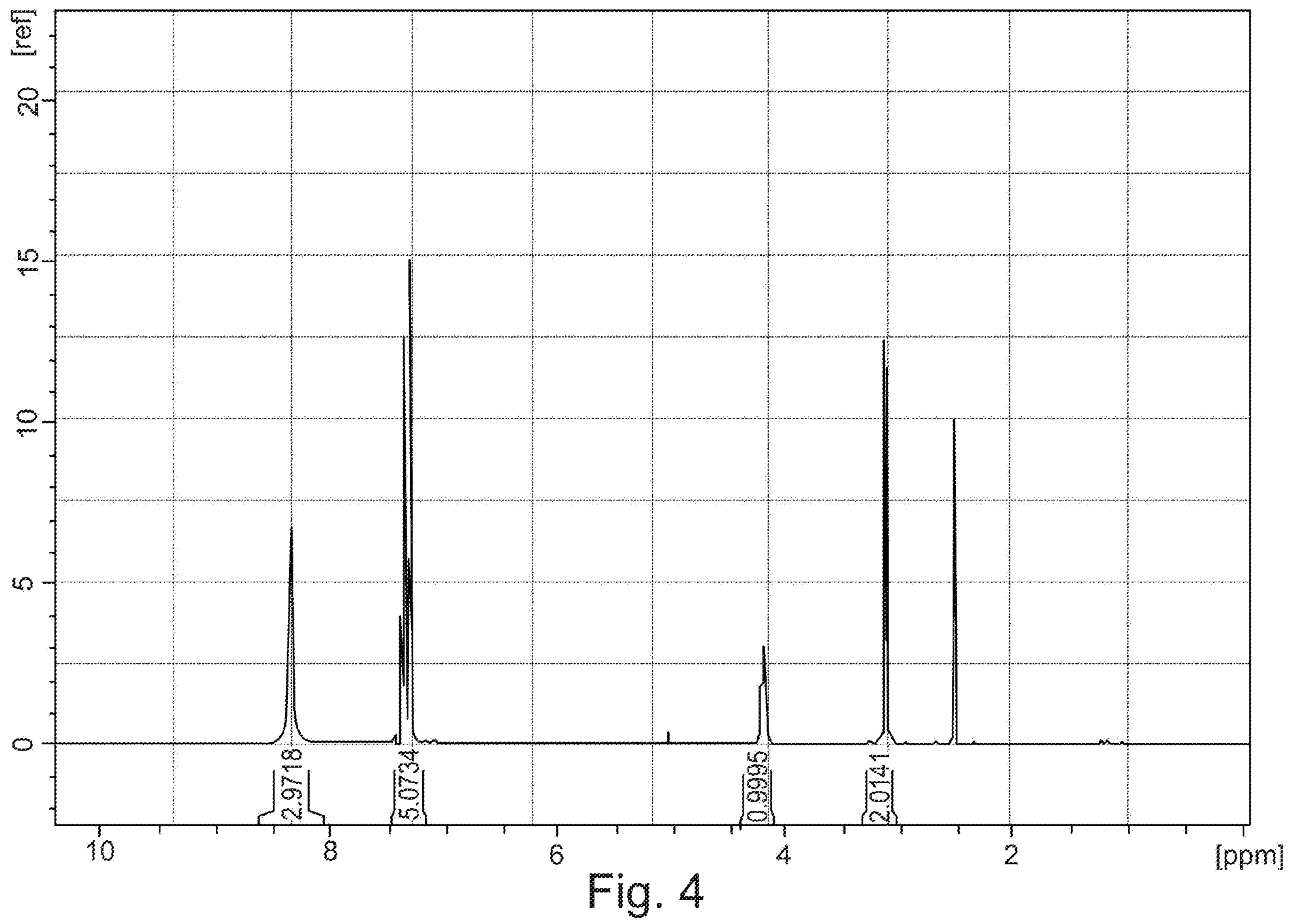
FIG. 4 shows the 1H NMR spectrum of D-phenylalanine according to Example 5.

25.9 grams of D-phenylalanine (93% yield) were thus obtained as a white solid. The product was analyzed by 1H NMR (400 MHz, DMSO-d6+TFA) according to the method described above. FIG. 4 shows the 1H NMR spectrum obtained, and the assignment of the related peaks is as follows: δ (ppm) 8.36 (bs, 3H, NH), 7.36-7.26 (m, 5H), 4.18 (t, 1H), 3.10 (d, 2H).

Example 6—Synthesis of D-Phenylalanine 7 grams of triethylamine (69.3 mmol) were slowly added, over 1 hour, to a suspension of D-phenylalanine:(R)-mandelic acid complex according to Example 1 (19.4 g, 63.02 mmol, 1 eq) in 196 mL of EtOH, while keeping the temperature between 20 and 30° C. After the addition was complete, the mixture was stirred at 25° C. for 4 hours and then filtered; the solid was washed with MeOH (2×20 mL) and dried at 40° C. for 72 hours. grams of D-phenylalanine (99% yield) were thus obtained as a white solid, whose identification and characterization by 1H NMR were carried out according to the method described above, obtaining results fully similar to those of D-phenylalanine according to Example 5.

Example 7—Synthesis of D-Phenylalanine 5 grams of triethylamine (50.0 mmol) were slowly added, over 1 hour, to a suspension of D-phenylalanine:(R)-mandelic acid complex according to Example 1 (14.4 g, 45.4 mmol, 1 eq) in 130 mL of MeOH, while keeping the temperature between 20 and 30° C. After the addition was complete, the mixture was stirred at 25° C. for 4 hours and then filtered; the solid was washed with MeOH (2×11 mL) and dried at 40° C. for 72 hours. 6.8 grams of D-phenylalanine (90% yield) were thus obtained as a white solid, whose identification and characterization by 1H NMR were carried out according to the method described above, obtaining results fully similar to those of D-phenylalanine according to Example 5.

Example 8—Synthesis of D-Phenylalanine 5 grams of triethylamine (50.0 mmol) were slowly added over 1 hour to a suspension of D-phenylalanine-(R)-mandelic acid complex according to Example 1 (14.4 g, 45.4 mmol, 1 eq) in 130 mL of MeOH, while keeping the temperature between 20 and 30° C. After the addition was complete, the mixture was stirred at 25° C. for 4 hours and then filtered; the solid was washed with MeOH (2×11 mL) and dried at 40° C. for 72 hours. 6.8 grams of D-phenylalanine (90% yield) were thus obtained as a white solid, whose identification and characterization by 1H NMR were carried out according to the method described above, obtaining results fully similar to those of D-phenylalanine according to Example 5.

Example 9—Synthesis of D-Phenylalanine 4 milliliters of a 30% by weight aqueous solution of $NH_3$ (60.0 mmol) were slowly added, over 30 minutes, to a suspension of D-phenylalanine-(R)-mandelic acid complex according to Example 1 (14.9 g, 47.0 mmol, 1 eq) in 145 mL of EtOH, while keeping the temperature between 20 and 30° C. After the addition was complete, the mixture was stirred at 25° C. for 4 hours and then filtered; the solid was washed with EtOH (2×15 mL) and dried at 40° C. for 72 hours. 7.5 grams of D-phenylalanine (95% yield) were thus obtained as a white solid, whose identification and characterization by 1H NMR were carried out according to the method described above, obtaining results fully similar to those of D-phenylalanine according to Example 5.

Example 10—Synthesis of D-Phenylalanine 4 milliliters of a 30% by weight aqueous solution of $NH_3$ (60.0 mmol) were slowly added, over 30 min, to a suspension of D-phenylalanine-(R)-mandelic acid complex according to Example 1 (14.6 g, 46.0 mmol, 1 eq) in 90 mL of MeOH, while keeping the temperature between 20 and 30° C. After the addition was complete, the mixture was stirred at 25° C. for 4 hours and then filtered; the solid was washed with MeOH (2×9 mL) and dried at 40° C. for 72 hours. 6.4 grams of D-phenylalanine (85% yield) were thus obtained as a white solid, whose identification and characterization by 1H NMR were carried out according to the method described above, obtaining results fully similar to those of D-phenylalanine according to Example 5.

Example 11—Synthesis of D-Phenylalaninol 10.4 grams of D-phenylalanine obtained according to Example 5 (63.0 mmol, 1 eq) were suspended in 110 grams of anhydrous THF, under a $N_2$ atmosphere. The suspension was heated to 35° C. and $NaBH_4$ (2.5 g, 66.1 mmol, 1.05 eq) was added. After the last addition, the reaction mixture was kept under stirring at the same temperature for another hour until no gas evolution was detected anymore. 20.3 grams of $BF_3$-THF complex (144.6 mmol, 2.3 eq) were then added over 3 hours while keeping the temperature at 35° C. At the end of the addition, the reaction mixture was still kept at the same temperature for a further 2 hours, then water (7.0 g) was added to quench the reaction and stirring was continued for a further 1 hour, while keeping the temperature at 35° C., detecting the evolution of H2. The resulting mixture was stirred at the same temperature for another 30 minutes, then 10% w/w NaOH (100 g) was slowly added over 1 hour. The reaction was kept under stirring at 55° C. for 6 hours, then the organic solvent was distilled and replaced with MeTHF (100 g). The obtained biphasic mixture was still kept under stirring at the same temperature and separated. The aqueous layer was extracted with additional MeTHF (100 g). Finally, the combined organic layers were washed with 50 grams of a solution obtained by combining 1 part by volume of a 10% by weight aqueous solution of NaOH and 1 part by volume of a 20% by weight aqueous solution of NaCl.

After concentration of the solvent and crystallization from toluene, 8.0 grams of D-phenylalaninol (85% yield) were obtained as a colorless crystal. The product was analyzed by chiral HPLC and by 1H NMR (400 MHz, DMSO-d6+TFA) according to the methods described above.

Figure 5:
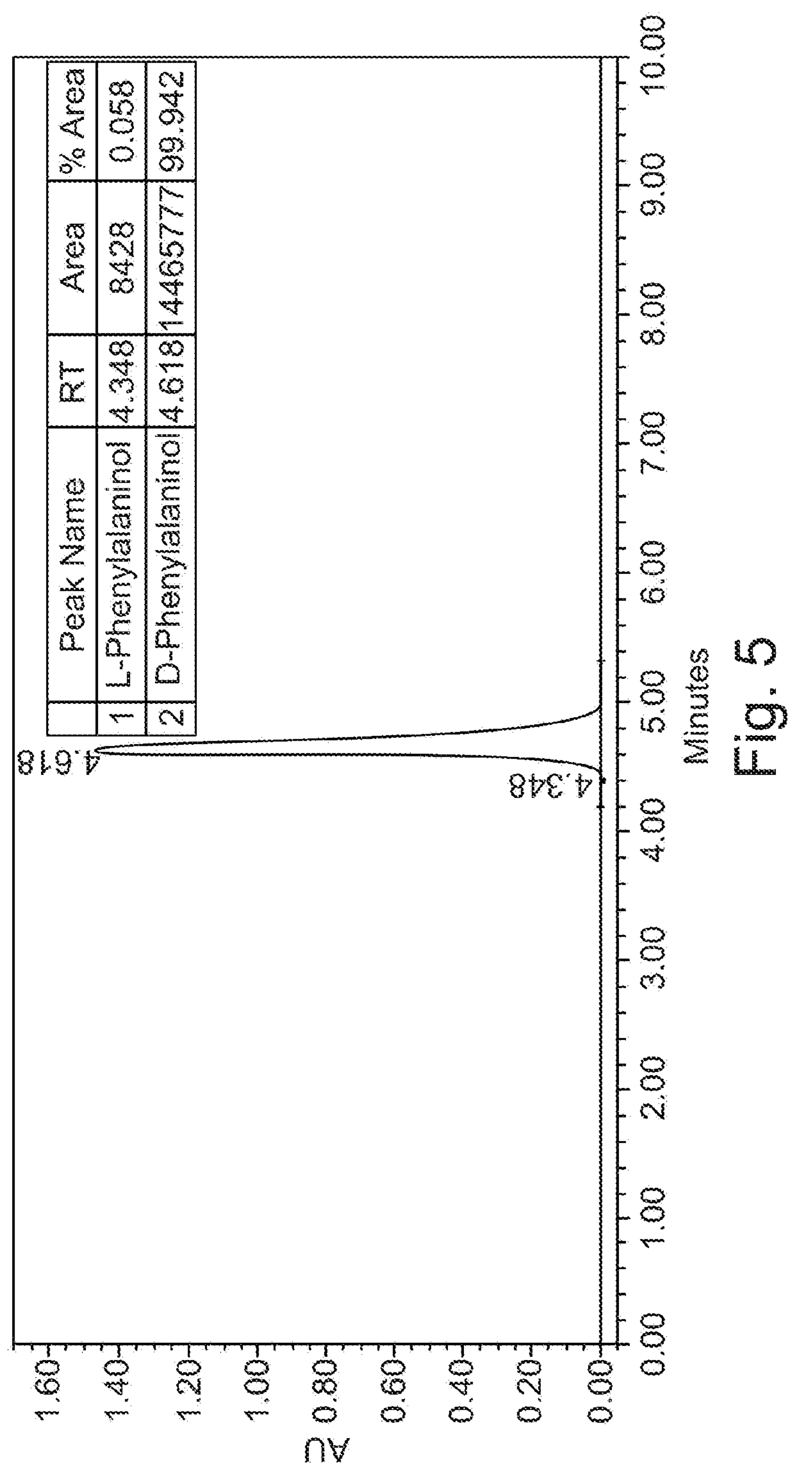
FIG. 5 shows the HPLC chromatogram of D-phenylalaninol obtained according to Example 11.

FIG. 5 shows the HPLC chromatogram obtained, in which the peak corresponding to (D)-phenylalaninol (RT 4.618) is present and in which it is possible to detect the substantial absence of the peak corresponding to (L)-phenylalaninol (RT 4.348) and the negligible percentage area of the same with respect to D-phenylalaninol.

Figure 6:
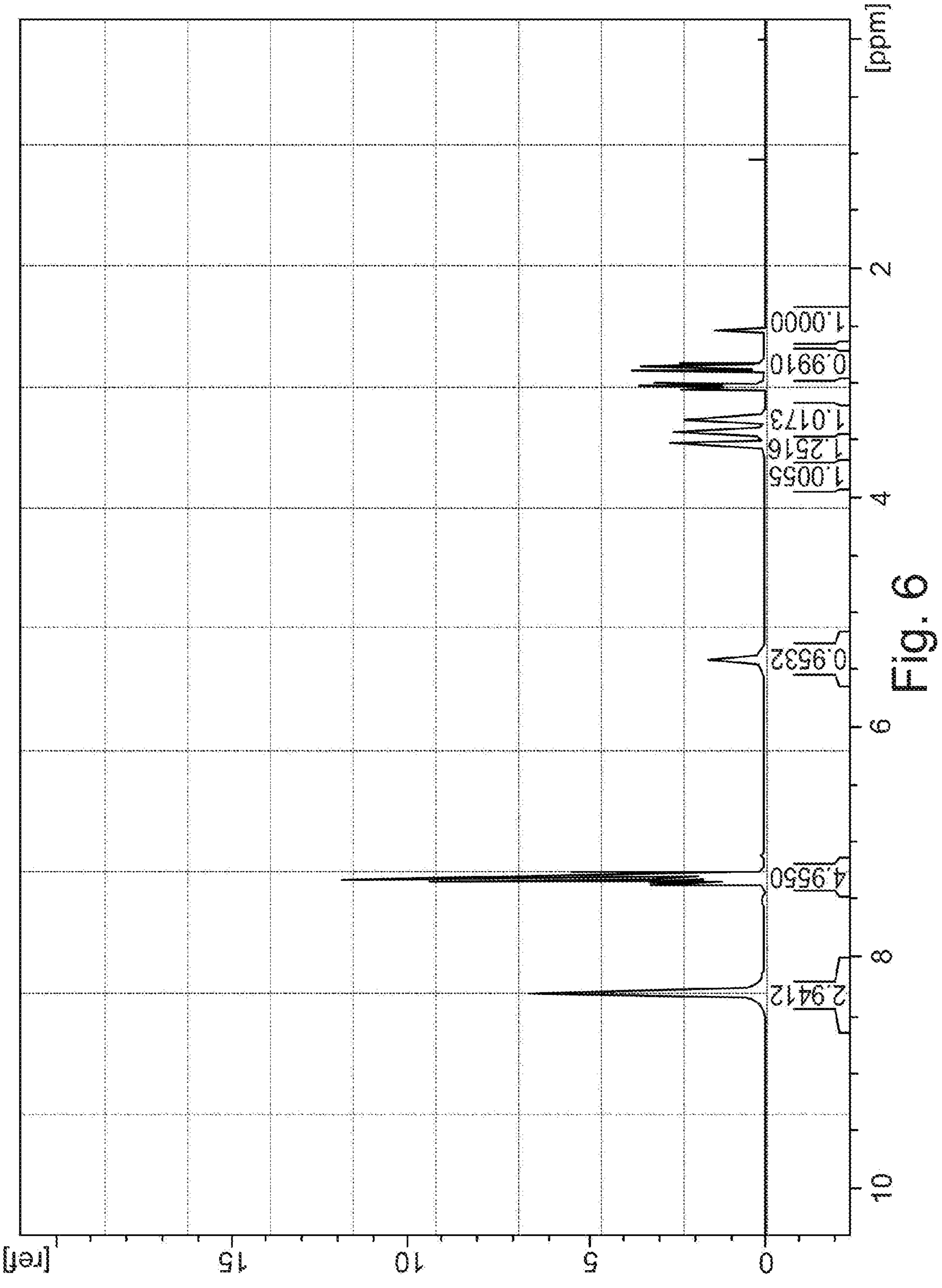
FIG. 6 shows the 1H NMR spectrum of D-phenylalaninol according to Example 11.

FIG. 6 shows the 1H NMR spectrum obtained and then relative peaks assignment: δ (ppm) 8.29 (bs, 3H, NH), 7.35-7.23 (m, 5H), 5.39 (bs, 1H, OH), 3.51 (m, 1H), 3.40 (m, 1H), 3.30 (m, 1H), 3.00 (m, 1H), 2.82 (m, 1H).

Example 12—Synthesis of D-Phenylalaninol 12.9 grams of D-phenylalanine (78.1 mmol, 1 eq) were suspended in 130 grams of anhydrous THF under a $N_2$ atmosphere. 25.1 grams of $BF_3$-THF complex (179.6 mmol, 2.3 eq) were added over 20 minutes, while keeping the temperature at 25° C. The reaction mixture was heated to 35° C. and the mixture stirred for 30 minutes, then $NaBH_4$ (3.0 g, 81.7 mmol, 1.05 eq) was added. After the last addition, the reaction mixture was kept under stirring at the same temperature for a further 2 hours, then water (10 g) was added to quench the reaction and stirring was continued for a further 1 hour, while keeping the temperature at 35° C., observing evolution of H2. The obtained mixture was kept under stirring at the same temperature for another 30 minutes, then 10% w/w NaOH (120 g) was slowly added over 1 hour. The reaction was kept under stirring at 55° C. for 6 hours, then the organic solvent was distilled and replaced with MeTHF (140 g). The resulting biphasic mixture was kept under stirring at the same temperature and separated. The aqueous layer was extracted with additional MeTHF (140 g). Finally, the combined organic layers were washed with 70 grams of a solution obtained by combining 1 part by volume of a 10% by weight aqueous solution of NaOH and 1 part by volume of a 20% by weight aqueous solution of NaCl. After concentration of the solvent and crystallization from toluene, 9.1 grams of D-phenylalaninol (77% yield) were obtained as a colorless crystal, whose identification and characterization by HPLC and by 1H NMR was carried out according to the methods described above, obtaining results fully similar to those of D-phenylalaninol according to Example 11.

Example 13—Synthesis of D-Phenylalaninol 4.0 grams of D-phenylalanine (24.2 mmol, 1 eq) were suspended in 40 grams of anhydrous THF, under a $N_2$ atmosphere. 3.4 grams of $BF_3$-THF complex (24.2 mmol, 1.0 eq) were added over 10 minutes, while keeping the temperature at 25° C. The reaction mixture was heated to 35° C. and stirred for 1 hour, and 0.95 grams of $NaBH_4$ (25.2 mmol, 1.05 eq) were added over 2 hours. After the last addition, the reaction mixture was kept under stirring at the same temperature for a further 1 hour, then further $BF_3$-THF complex (4.1 g, 29.1 mmol, 1.3 eq) was added over 2 hours, while keeping the temperature at 35° C. After the last addition, the reaction mixture was kept under stirring at the same temperature for another 2 hours, then water (3 g) was added to quench the reaction and stirring was continued for a further 1 hour, while keeping the temperature at 35° C. The resulting mixture was kept under stirring at the same temperature for another 30 minutes, then a 10% by weight aqueous solution of NaOH (35 g) was slowly added over 1 hour. The resulting mixture was kept under stirring at ° C. for 6 hours, then the organic solvent was distilled and replaced with MeTHF (40 g). The biphasic mixture obtained was kept under stirring at the same temperature and separated. The aqueous layer was extracted with additional MeTHF (40 g). Finally, the combined organic layers were washed with 18 grams of a solution obtained by combining 1 part by volume of a 10% by weight aqueous solution of NaOH and 1 part by volume of a 20% by weight aqueous solution of NaCl. After concentration of the solvent and crystallization from toluene, 2.8 grams of D-phenylalaninol (75% yield) were obtained as a colorless crystal, whose identification and characterization by HPLC and by 1H NMR were carried out according to the methods described above, obtaining results fully similar to those of D-phenylalaninol according to Example 11.

Example 14—Synthesis of (2R)-2-amino-3-phenylpropylcarbamate 8.0 grams of D-phenylalaninol (52.9 mmol, 1.0 eq) and 6.9 grams of sodium cyanate (105.8 mmol, 2.0 eq) were suspended in 160 milliliters of anhydrous DCM and the reaction mixture was cooled to 0-5° C. with a ice bath. 17.8 grams of methanesulfonic acid (185.2 mmol, 3.5 eq) were slowly added, over 3 hours, while keeping the temperature below 5° C. After the addition, the reaction mixture was allowed to warm to 25° C. and kept under stirring at the same temperature for 20 hours, then a 10% by weight aqueous solution of NaOH was added to quench the reaction, while keeping the temperature below 5° C. and until reaching a pH of 10-12. The two layers were then brought back to 25° C. and then separated. The aqueous layer was extracted with DCM (2×100 mL). The combined organic layers were washed with a 20% by weight aqueous solution of sodium chloride, dried over $Na_2SO_4$, filtered and concentrated. 8.1 grams of (2R)-2-amino-3-phenylpropylcarbamate (79% yield) were thus obtained as a colorless oil, which were used without further purification.

Example 15—Synthesis of (2R)-2-amino-3-phenylpropylcarbamate 10.0 grams of D-phenylalaninol (65.6 mmol, 1.0 eq) and 8.6 grams of sodium cyanate (131.4 mmol, 2.0 eq) were suspended in 250 milliliters of anhydrous DCM and the reaction mixture was cooled to −5° C. with an ice and salt bath. Anhydrous HCl (10 eq) was bubbled for 3 hours, while keeping the temperature below 0° C. After the addition, the reaction mixture was allowed to warm to 25° C. and kept under stirring at the same temperature for a further 2 hours; a 10% by weight aqueous solution of NaOH was added to quench the reaction, while keeping the temperature below 5° C. and until a pH of 10-12 is reached. The two layers were then brought back to 25° C., and then separated. The aqueous layer was extracted with DCM (2×100 mL). The combined organic layers were washed with a 20% by weight aqueous solution of sodium chloride, dried over $Na_2SO_4$, filtered and concentrated. 10.9 grams of (2R)-2-amino-3-phenylpropylcarbamate (85% yield) were thus obtained as a colorless oil, which were used without further purification.

Example 16—Synthesis of (2R)-2-amino-3-phenylpropylcarbamate hydrochloride 8.5 grams of (2R)-2-amino-3-phenylpropylcarbamate according to Example 14 were dissolved in 45 milliliters of anhydrous isopropanol and the resulting mixture was heated to 40° C. Gaseous HCl (5 eq) was then bubbled into the mixture, while keeping the temperature below 60° C. The reaction was kept under stirring at 60° C. for a further 2 hours, then allowed to cool to 20° C. and further stirred for 1 hour before recovering the solid by filtration. The filter cake was washed with 10 milliliters of isopropanol and dried in vacuo to give (2R)-2-amino-3-phenylpropylcarbamate hydrochloride as a white crystalline solid (9.0 g, 90% yield).

Figure 7:
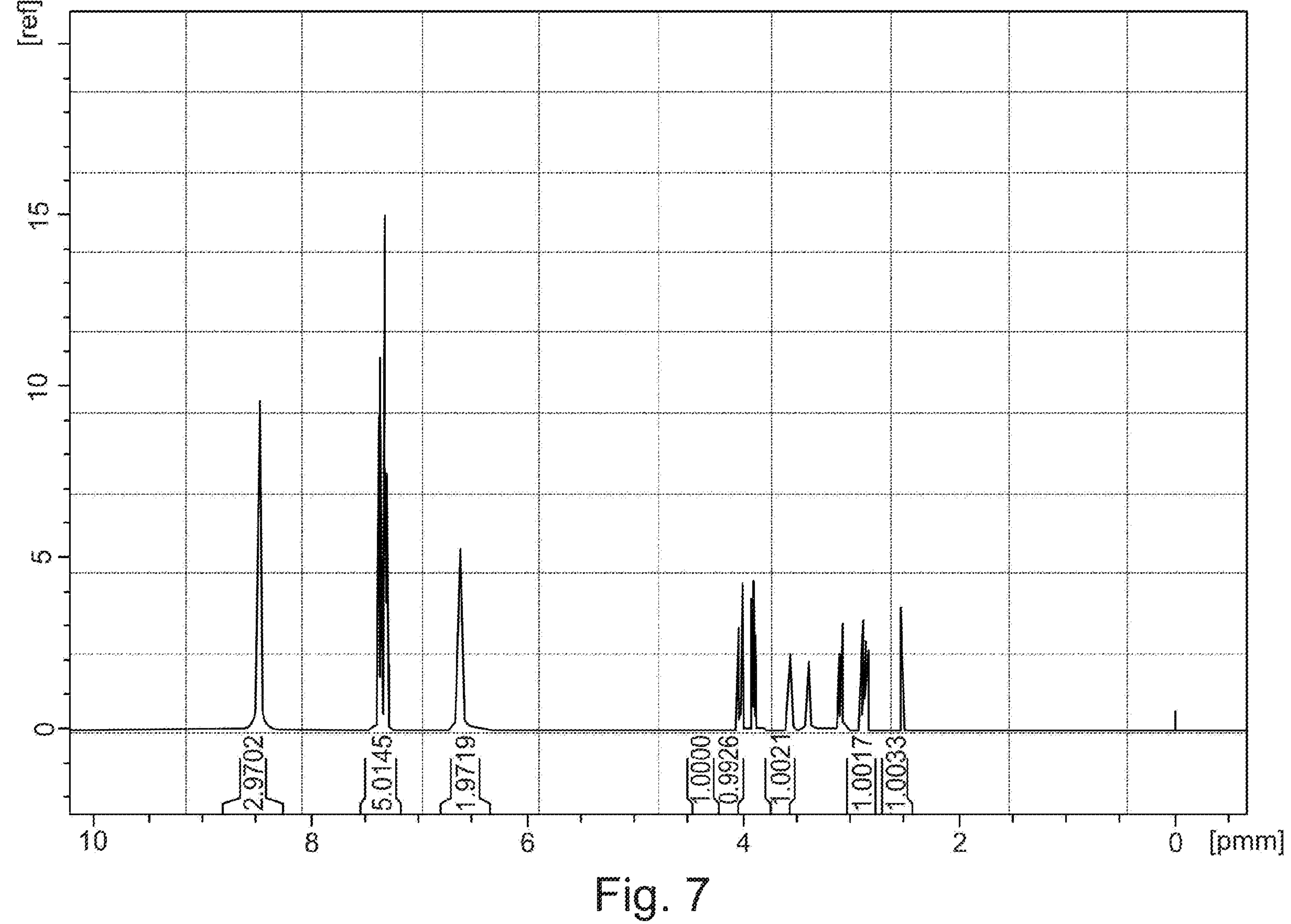
FIG. 7 shows the 1H NMR spectrum of (2R)-2-amino-3-phenylpropylcarbamate hydrochloride (solriamfetol hydrochloride) according to Example 16.

FIG. 7 shows the 1H NMR spectrum obtained, and the relative peaks assignment is as follows: δ (ppm) 8.46 (bs, 3H, NH), 7.37-7.25 (m, 5H), 6.60 (bs, 2H, NH), 4.01 (m, 1H), 3.88 (m, 1H), 3.53 (m, 1H), 3.80 (m, 1H), 2.86 (m, 1H).

Figure 8:
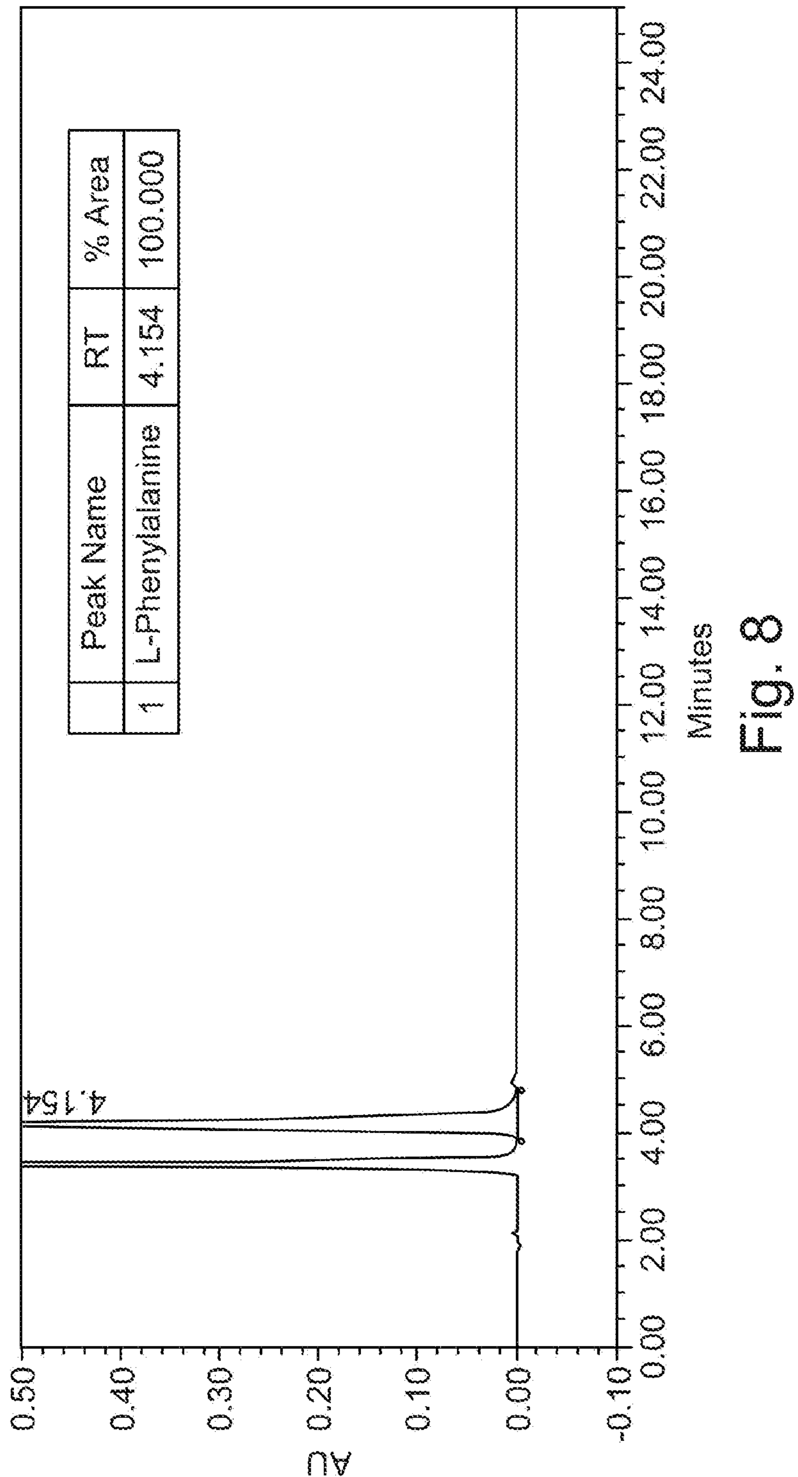
FIG. 8 shows the HPLC chromatogram of the solid obtained according to Example 17 (comparative)

Example 17 (Comparative)—Replication of Example 1 in the Absence of Salicylaldehyde Example 1 was repeated without adding salicylaldehyde. The solid obtained after filtration of the reaction mixture, subsequent washing with acetic acid and drying, was analyzed by chiral HPLC and did not show the formation of the D-phenylalanine:(R)-mandelic acid complex. FIG. 8 shows the HPLC chromatogram obtained, in which only the peak corresponding to (L)-phenylalanine (RT 4.154) is present.

The test performed, when compared with Example 1, therefore confirmed the relevance of the aldehyde presence in the reaction mixture to obtain the D-phenylalanine:(R)-mandelic acid complex starting from L-phenylalanine under the investigated reaction conditions.

Example 18 (Comparative)—Replication of the Process Described in "Optical Separation of Racemic Phenyl Alanine and Structure of Complex Consisting of R-Phenyl Alanine and Mandelic Acid", Chinese J. Struct. Chem. Vol. 23, No. 1, Pages 38-40

The racemic phenylalanine separation process described in the publication "Optical separation of racemic phenyl alanine and structure of complex consisting of R-phenyl alanine and mandelic acid", Chinese J. Struct. Chem. vol. 23, no. 1, pages 38-40, was replicated starting from 8.4 grams of DL-phenylalanine racemic mixture (Fluorochem, product code 093728), in order to verify the reaction yield and to determine the diastereoisomeric ratio of the D-phenylalanine:(R)-mandelic acid complex obtained.

Figure 9:
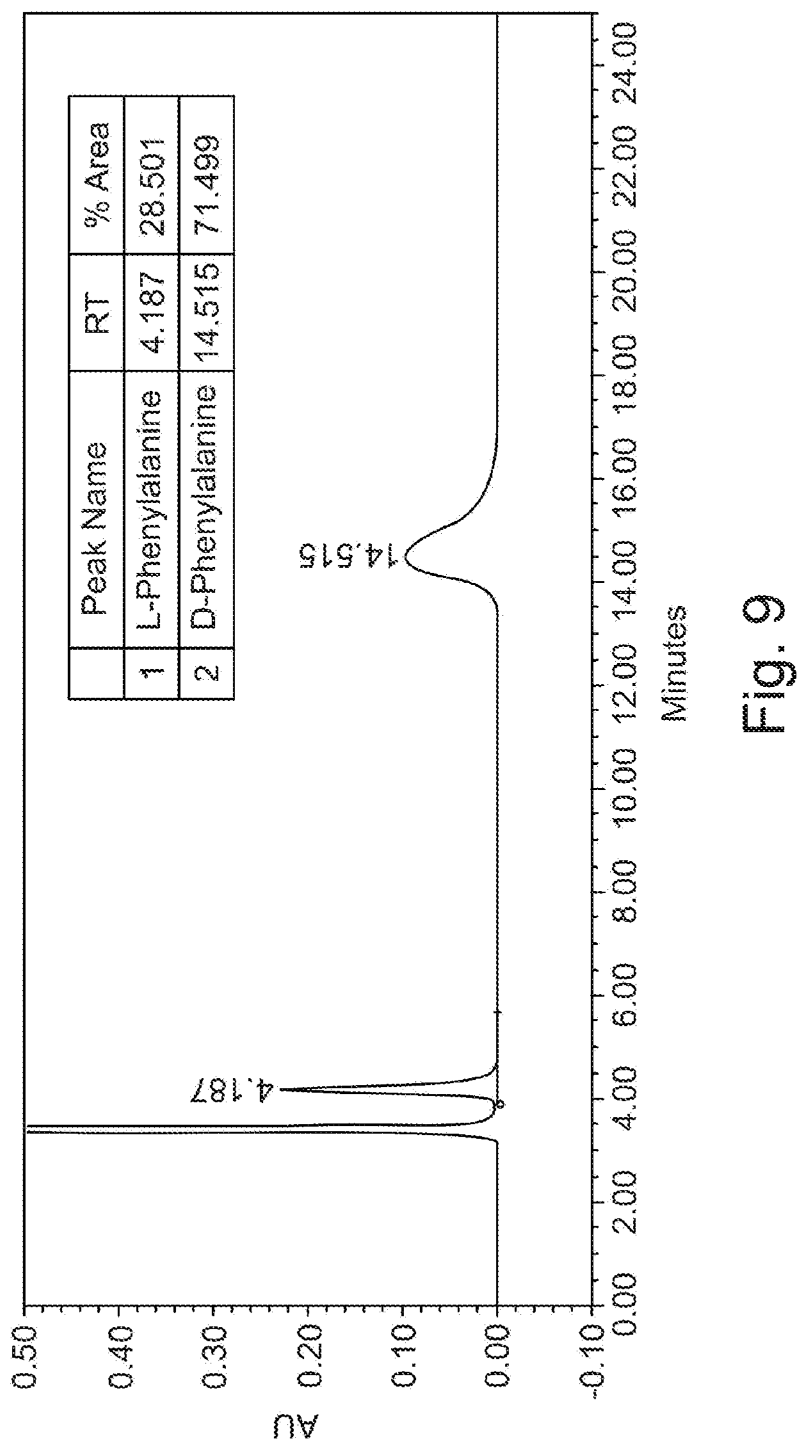
FIG. 9 shows the HPLC chromatogram of the D-phenylalanine:(R)-mandelic acid complex after filtration, washing and drying of the solid obtained from the reaction mixture according to Example 18 (comparative)

In particular, 8.4 grams of DL-phenylalanine racemic mixture and 10.2 grams of (R)-mandelic acid were dissolved in 200 milliliters of hot water. The solution was slowly cooled and brought to room temperature, obtaining 9.0 grams of a white solid after one day. The solid was analyzed by chiral HPLC (FIG. 9) observing the formation of the D-phenylalanine:(R)-mandelic acid complex (6.4 g, 41.2% yield, diastereoisomeric ratio (d.r.)=71.5/28.5).

Figure 10:
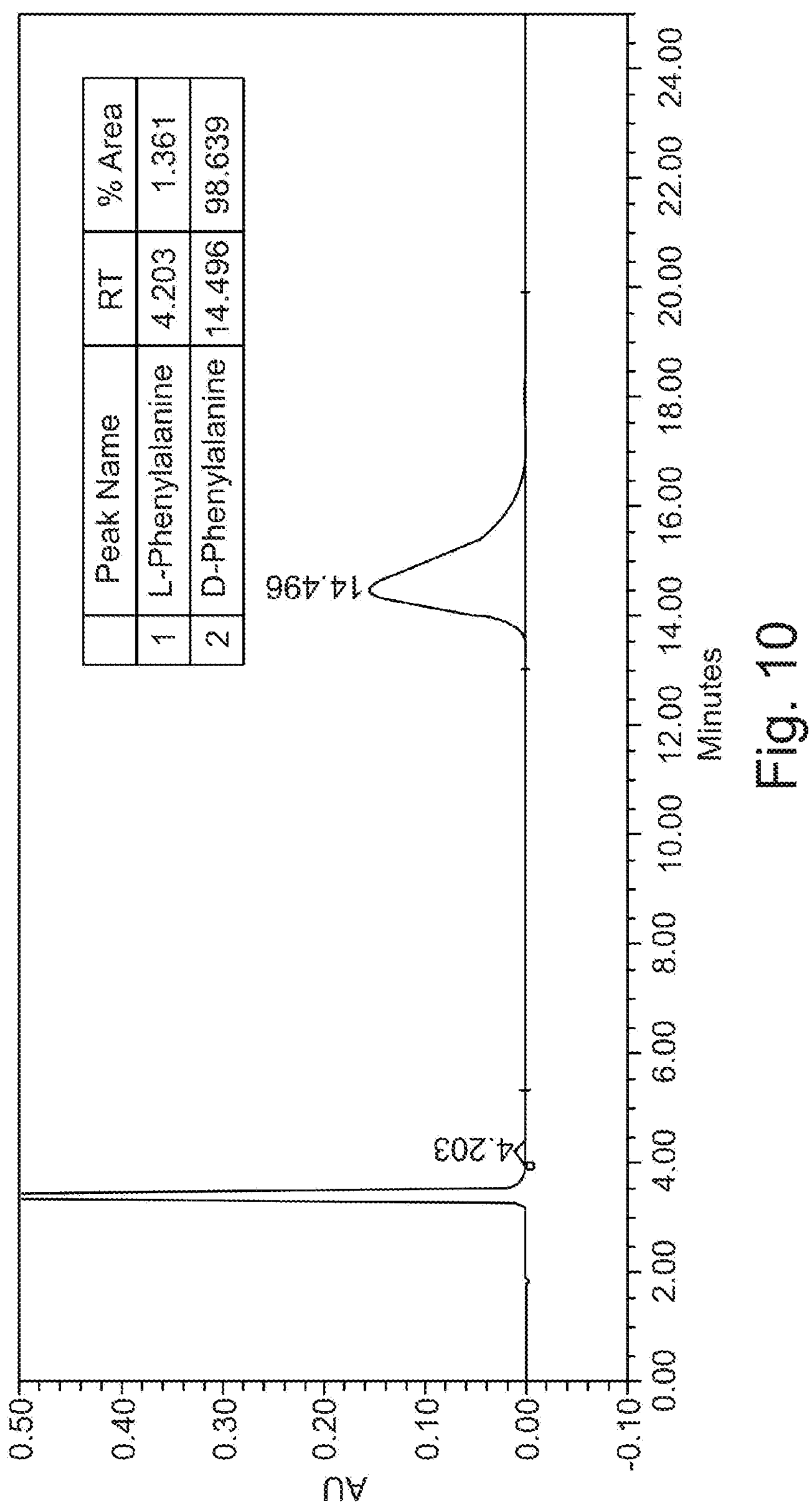
FIG. 10 shows the HPLC chromatogram of the D-phenylalanine:(R)-mandelic acid complex obtained after recrystallization in aqueous solution of the solid obtained from the reaction mixture according to Example 18 (comparative).

The solid was then recrystallized in aqueous solution, isolating by filtration 2.0 grams of white solid which was also analyzed by chiral HPLC (FIG. 10), observing the obtaining of D-phenylalanine:(R)-mandelic acid complex with a diastereoisomeric ratio of 98.6/1.4, with an overall reaction yield of 12.8%.

The test performed, when compared with step a. of the process according to the present invention, confirmed that in the absence of aldehyde, even starting from a DL-phenylalanine racemic mixture, the D-phenylalanine:(R)-mandelic acid complex can be obtained but with a much lower reaction yield, and with diastereoisomeric ratio values similar to those obtained in the process according to the invention only after a subsequent purification step, thus inevitably further lowering the yield to values that jeopardize the productivity of the same process.

The invention claimed is:

1. A process for preparing (2R)-2-amino-3-phenylpropylcarbamate hydrochloride of formula (I)

(I)

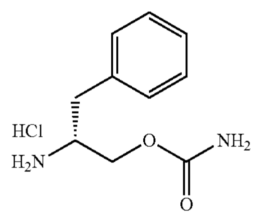

comprising the steps of:

a. adding (R)-mandelic acid and at least one aldehyde to a suspension of L-phenylalanine in acetic acid, thus obtaining a D-phenylalanine: (R)-mandelic acid complex, wherein the D-phenylalanine: (R)-mandelic acid molar ratio is 1:1;

b. isolating the D-phenylalanine of formula (II)

(II)

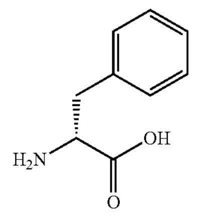

from the D-phenylalanine: (R)-mandelic acid complex obtained from step a;

c. reacting the D-phenylalanine obtained from step b. with a reducing agent, thus obtaining (R)-(+)-2-amino-3-phenyl-1-propanol of formula (III)

(III)

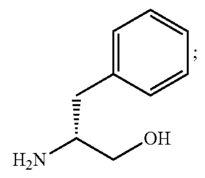

d. reacting (R)-(+)-2-amino-3-phenyl-1-propanol obtained from step c. with an acid thus obtaining (2R)-2-amino-3-phenylpropilcarbamate of formula (IV)

(IV)

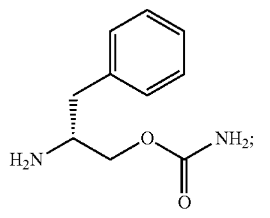

e. converting (2R)-2-amino-3-phenylpropilcarbamate obtained from step d. into said (2R)-2-amino-3-phenylpropylcarbamate hydrochloride of formula (I).

2. The process according to claim 1, wherein said step b. comprises adding at least one base to a solution of said complex in at least one polar solvent.

3. The process according to claim 1, wherein said step c. comprises reacting the D-phenylalanine obtained from step b. with a reducing system consisting of sodium borohydride and boron trifluoride, wherein said sodium borohydride is used in an amount comprised between 1 and 1.2 equivalents with respect to said D-phenylalanine.

4. The process according to claim 1, wherein said step c. comprises crystallizing said (R)-(+)-2-amino-3-phenyl-1-propanol.

5. The process according to claim 1, wherein in said step d. the reaction between (R)-(+)-2-amino-3-phenyl-1-propanol obtained from step c. and an acid occurs in an anhydrous organic solvent.

6. The process according to claim 1, wherein said step e. comprises bubbling gaseous HCl into a solution of said (2R)-2-amino-3-phenylpropylcarbamate in a polar protic solvent.

7. A process for preparing a D-phenylalanine: (R)-mandelic acid complex, wherein the D-phenylalanine: (R)-mandelic acid molar ratio is 1:1, comprising adding (R)-mandelic acid and at least one aldehyde to a suspension of L-phenylalanine in acetic acid.

8. A process for preparing D-phenylalanine of formula (II)

(II)

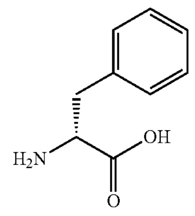

comprising the steps of:

i. adding (R)-mandelic acid and at least one aldehyde to a suspension of L-phenylalanine in acetic acid, thus obtaining a D-phenylalanine: (R)-mandelic acid complex, wherein the D-phenylalanine: (R)-mandelic acid molar ratio is 1:1; and ii. isolating D-phenylalanine from D-phenylalanine: (R)-mandelic acid complex obtained from step i.

* * * * *